United States Patent [19]
Hille et al.

[11] Patent Number: 6,114,347
[45] Date of Patent: Sep. 5, 2000

[54] PHARMACEUTICAL FORMULATION FOR THE PROPHYLAXIS AND PRETREATMENT OF A POISONING CAUSED BY ORGANOPHOSPHORUS CHOLINESTERASE INHIBITORS

[75] Inventors: Thomas Hille; Walter Müller, both of Neuwied; Bodo Asmussen, Ammersbek, all of Germany; Aharon Levy, Hanan; Yacov Meshulam, Ramat-Gan, both of Israel

[73] Assignees: LTS Lohmann Therapie-Systeme GmbH, Neuwied, Germany; Israel Institute for Biological Research, Ness-Ziona, Israel

[21] Appl. No.: 08/656,207
[22] PCT Filed: Dec. 6, 1994
[86] PCT No.: PCT/EP94/04049
  § 371 Date: Aug. 23, 1996
  § 102(e) Date: Aug. 23, 1996
[87] PCT Pub. No.: WO95/15756
  PCT Pub. Date: Jun. 15, 1995

[30] Foreign Application Priority Data

Dec. 10, 1993 [DE] Germany .............. 43 42 173

[51] Int. Cl.[7] .......... A61K 31/44; A61K 31/40; A61K 31/27
[52] U.S. Cl. .......... 514/297; 514/304; 514/346; 514/411; 514/479; 514/823
[58] Field of Search .............. 514/297, 304, 514/346, 411, 479, 823

[56] References Cited

U.S. PATENT DOCUMENTS

| | | | |
|---|---|---|---|
| 3,760,805 | 9/1973 | Higuchi | 128/260 |
| 3,760,806 | 9/1973 | Leeper | 128/260 |
| 3,764,984 | 10/1973 | McCartney | 340/168 S |
| 3,845,770 | 11/1974 | Theeuwes et al. | 128/260 |
| 3,916,899 | 11/1975 | Theeuwes et al. | 128/260 |
| 3,987,790 | 10/1976 | Eckenhoff et al. | 128/260 |
| 4,137,300 | 1/1979 | Sheth et al. | 424/21 |

FOREIGN PATENT DOCUMENTS 4115558  11/1992  Germany .

OTHER PUBLICATIONS

Lim et al., Pharmacol. Biochem. Behav., vol. 31, No. 3, pp. 633–640, 1988.

Lenrox et al., Drug and Chemical Toxicology, 15(4), 271–283, 1992.

"Dealkylation as a Mechanism for Aging of Cholinesterase After Poisoning with Pinacolyl Methylphosphonofluoridate," Fleisher et al., Biochemical Pharmacology, vol. 14, pp. 641–650, 1965.

"The Use of Carbamates and Atropine in the Protection of Amimals Against Poisoning by 1,2,2–Trimethylpropyl Methylphosphonofluoridate," Berry et al., Biochemical Pharmacology, vol. 19, pp. 927–934, 1970.

"When All Else Fails," Leadbeater, Chemistry in Britain, pp. 683–688, Jul. 1988.

Primary Examiner—Kimberly Jordan
Attorney, Agent, or Firm—Wenderoth, Lind & Ponack, L.L.P.

[57] ABSTRACT

A pharmaceutical formulation for the prophylaxis and preliminary treatment of a poisoning caused by organophosphorus cholinesterase inhibitors is characterized in that it consists of an active substance combination of at least one parasympathomimetic and at least one parasympatholytic.

16 Claims, No Drawings

PHARMACEUTICAL FORMULATION FOR THE PROPHYLAXIS AND PRETREATMENT OF A POISONING CAUSED BY ORGANOPHOSPHORUS CHOLINESTERASE INHIBITORS

This application is a 371 of PCT/EP94/04049, filed Dec. 6, 1994.

BACKGROUND OF THE INVENTION

The present invention relates to a pharmaceutical formulation for the prophylaxis or preliminary treatment of a poisoning caused by organophosphorus cholinesterase inhibitors.

The present invention is to provide pharmaceutical formulations releasing suitable active substances in a controlled manner for the prophylactic treatment of poisonings caused by cholinesterase inhibitors. Examples of organophosphorus cholinesterase inhibitors include esters of phosphoric acid derivatives, e.g., nitrostigmine (=diethyl-(4-nitrophenyl)-thiophosphate, better known under the names Parathion or E 605), but they also include tabun, as well as the phosphonic acid derivatives sarin, soman and VX.

Among other things cholinesterase-inhibiting phosphoric esters are used as insecticides in agriculture. Since they also have a toxic effect on human beings, the staff working in agriculture is subject to a basic hazard to life and limb; this is true all the more since these organic phosphoric esters can also be absorbed via the skin. As compared to insecticides, the compounds tabun, sarin, soman and VX which belong to the group of the so-called nerve warfare agents are distinguished by a particularly high toxicity. All of these compounds are more or less strong inhibitors of the acetylcholinesterase, an enzyme which physiologically blocks the effect of the transmitter acetylcholine released at certain nerve endings. Most of the symptoms of poisoning caused by cholinesterase inhibitors are produced by an inundation with endogenic acetylcholine.

The basic drug therapy of such a poisoning consists in the administration of the parasympatholytic atropine, blocking the exceeding muscarinic acetylcholine effects (e.g., increase of secretion in the respiratory system, bronchospasm, inhibition of the central nervous respiratory drive). There is no suitable antagonist available to normalize the exceeding nicotinic acetylcholine actions (e.g., inhibition of the impulse transmission at the synapses of motorial nerves to the respiratory musculature and to other skeletal muscles up to a complete peripheral motor paralysis). The peripherally caused myoparesis can only be compensated by oximes, e.g., pralidoxime (PAM) or obidoxime (Toxogonin®) whose mechanism of action consists in a reactivation of the inhibited acetylcholinesterase.

Some of the phosphoric cholinesterase inhibitors are distinguished by the fact that they split off alkyl residues after accumulation to the acetylcholinesterase, thus stabilizing the bond ("aging"). The aged esterase inhibitor complex cannot be reactivated by oximes. In case of poisonings caused by the nerve warfare agent soman, aging already occurs after 2 to 5 minutes. The therapy with atropine and oximes is absolutely insufficient in case of a soman poisoning. The effectiveness of atropine and oximes can considerably be improved by a preliminary treatment with indirect parasympathomimetics, e.g., carbamic acid esters, such as pyridostigmine and physostigmine. Carbamic acid esters inhibit the acetylcholinesterase in a manner similar to that of phosphoric esters. However, the bond is of a shorter duration and completely reversible. The fact that the carbamates inhibit part of the acetylcholinesterase, if dosed suitably, and thus remove it from the reach of the phosphoric esters and phosphonates having a stronger and prolonged inhibition may well be a decisive factor for their protective action, provided that the pretreatment started in time.

Also, the treatment of a poisoning caused by organophosphorus insecticides requires prompt medical care in any case. Since medical care in case of harvesters cannot always be accomplished promptly, there is a need for drugs prophylactically counteracting an intoxication. The use of carbamic acid esters for this purpose has already been described (Leadbeater, L. Chem. in Brit. 24, 683, 1988). The same applies to the effectiveness of carbamic acid esters in the pretreatment of a soman poisoning in animal experiments (Fleischer, J. H., Harris, L. W. Biochem. Pharmacol. 14, 641, 1965, Berry, W. K., Davies, D. R. Biochem. Pharmacol, 19, 927, 1970). The effective dosage of drugs to be applied prophylactically must not impair reactivity and functional capacity. However, carbamic acid esters have a low therapeutic index. As compared to pyridostigmine, an increased protective action can be achieved by physostigmine, however, the side effects are more severe.

DE-OS 41 15 558 describes a prophylactic antidote consisting of a combination of pyridostigmine or physostigmine and N-methyl-4-piperidyl-1-phenylcyclopentane carboxylate-hydrochloride or arpenal, sycotrol, carmiphene or benactyzine, and, as an additional compelling component, a tranquilizer, i.e., diazepam or clonazepam. The undesired effects of physostigmine or pyridostigmine can therefore not be suppressed by the listed parasympatholytics alone, requiring the additional administration of tranquilizers which have side effects that are problematic.

BRIEF SUMMARY OF THE INVENTION

It is the object of the present invention to allow prophylactic administration of carbamic acid esters or other indirect parasympathomimetics at a dosage that results in a sufficient protection against organophosphorus cholinesterase inhibitors without causing undesired accompanying symptoms. According to the present invention, this object is achieved by a pharmaceutical formulation having an active substance combination of at least one parasympathomimetic and at least one parasympatholytic. This solution is most surprising since the present invention shows that the parasympatholytic not only contributes to the protective action but also reliably suppresses the undesired effects of the parasympathomimetic.

DETAILED DESCRIPTION OF THE INVENTION

Unlike the direct parasympathomimetics indirect parasympathomimetics do not act as agonists at the acetylcholine receptor. What is more, they prevent degradation of the acetylcholine by the fact that they inhibit the enzyme acetylcholinesterase, e.g., carbamic acid derivatives, such as physostigmine, heptylphysostigmine, neostigmine and pyridostigmine. Since the action of these substances is effected by the transmission of the carbamic acid, racemates are as effective as the genuine enantiomers. For this reason, the present invention also includes racemates. In addition, other acetylcholinesterase inhibitors are suitable, such as galanthamine or tetrahydroacridine or velnacridine; their mechanism of action is not based on the transmission of carbamic acid. The term parasympatholytic is understood to include substances having an affinity to muscarinic acetylcholine receptors without causing an effect. The following genuine alkaloids are mentioned as examples which are not intended to be limitative of the present invention, these include scopolamine (L-hyoscin) and L-hyoscyamine, their racemates, e.g., atropine, or their semi-synthetic derivatives, e.g., homatropine or N-butyl scopolamine. Additionally suitable are: completely synthetic parasympatholytics, such as benzatropine or benzetinmide. Other parasympathomimetics or parasympatholytics are known to those skilled in the art. It is not only the choice of the drugs that is decisive but also the fact that they are released from the administration form in a controlled and matched manner.

Administration forms releasing active substances in a controlled manner are already known in the art. The administration of pharmaceutically effective compounds by means of such formulations may be effected orally or in another manner, e.g., parenterally.

Formulations for the oral administration which are suitable within the scope of the present invention will be described briefly in the following. In one of these formulations the pharmaceutic active substance is encapsulated in a semi-permeable membrane, e.g., in cellulose acetate. A tiny hole is pierced into the capsule material by means of a drill or laser jet. Water is absorbed through the material of the capsule in the patient's gastrointestinal tract. By means of osmotic pressure the pharmaceutic active substance is driven through the tiny aperture in the desired gradual, constant and controlled manner. Such systems are described in U.S. Pat. Nos. 3,760,805, 3,760,806, 3,764,984, 3,845,770, 3,916,899, and 3,987,790. The pharmaceutic active substances in these systems may be present in solid form or absorbed to ion exchange resins.

Another system for the oral administration according to the present invention is described by Sheth and Leeson in U.S. Pat. No. 4,137,300. This patent describes a formulation comprising a wax matrix.

The active substances according to the present invention are administered by means of a corresponding formulation in an appropriate and suitable manner. The solid active substances may be administered in solution or as suspension. The solution or suspension medium may be aqueous or organic. Suitable solution or suspension media for drugs include, for example, water, silicone fluid or mineral oil.

In order to facilitate the administration of a compound by means of a formulation as described above, a free-flow agent may be added to the system. Some suitable free-flow agents for oral formulations include, for example, polyethylene glycol, hydroxypropyl methyl cellulose and sugar.

Formulations suitable for the application of active substances are those allowing a depot effect of the active substance. In this connection the formulation is applied as injectable solution on a nonaqueous basis. The suitable solvents are known to those skilled in the art. The following vegetable oils which are prescribed by some pharmacopeias are mentioned to illustrate, but not to limit the present invention: Peanut oil, olive oil, almond oil, sunflower oil, soybean oil, and sesame oil are of major importance. Castor oil frequently has a particularly favorable solubility for drugs; additionally suitable are oils of animal origin.

The oils are physiologically indifferent and well tolerated. To this end, they must be purified in a particular manner and have low acid and peroxide numbers. Since an intravenous application is not possible owing to the fact that they cannot be mixed with the blood serum and could lead to pulmonary embolism, they can only be used for intramuscular and subcutaneous injection preparations. Oily solutions and suspensions remain at the site of application for a relatively long period of time (often up to 1 month) and release the active substances in a protracted manner.

The present invention will be illustrated by means of the following examples:
Potency Test Based on Animal Experiments The protective effect of pyridostigmine and physostigmine alone and combined with scopolamine was tested on the basis of a soman poisoning in guinea pigs. 24 hours before the soman load, 6 to 10 animals received a pyridostigmine (3 $cm^2$/kg) or physostigmine (1.5 $cm^2$/kg) skin patch. After a 24-hour application of the physostigmine skin patch, plasma concentrations of 0.9±0.3 ng/ml (average value±SEM; n=4) were measured. When the larger pyridostigmine skin patch was applied, the cholinesterase activity in the total blood was inhibited by 38±4%, in case of the smaller physostigmine skin patch by 48±10%. In order to test the additional protective action of scopolamine either a commercial transdermal therapeutic system (Scopoderm® TTS) was used, or osmotic minipumps (Alzet®) having a release rate of 9 to 10 ng scopolamine hydrobromide per kg of body weight and hour were implanted subcutaneously into the animals. The results obtained after application of the pyridostigmine and physostigmine skin patches and a soman load of 1.5 $LD_{50}$ intramuscular are shown in Table 1.

The physostigmine pretreatment is not only effective in case of a poisoning by soman but also in case of a sarin poisoning: after a transdermal pretreatment with physostigmine—Scopoderm®-TTS and a load of 1.5 $LD_{50}$ sarin, 9 out of 10 guinea pigs survived without an additional post-exposure therapy.

The efficacy of the physostigmine pretreatment with and without scopolamine against soman was determined in an additional test series on guinea pigs, wherein an additional post-exposure therapy was applied using atropine sulfate and obidoxime chloride, based on the efficacy index (protective ratio=quotient of $LD_{50}$ with treatment and $LD_{50}$ without treatment) (Table 2).

TABLE 1

Protective action of different kinds of preliminary treatments in guinea pigs against a load of 1.5 $LD_{50}$ soman IM, without an additional post-exposure therapy

| Pretreatment | Lethality rate (24 h) |
| --- | --- |
| no | 10/10 |
| pyridostigmine transdermally (3 $cm^2$/kg) | 6/6 |
| pyridostigmine transdermally (1.5 $cm^2$/kg) + Alzet ®-scopolamine 10 ng/$kg^{-1}h^{-1}$ | 5/6 |
| physostigmine transdermally (1.5 $cm^2$/kg) | 6/20 |
| physostigmine transdermally (1.5 $cm^2$/kg) + Alzet ®-scopolamine 9 ng/$kg^{-1}h^{-1}$ | 0/10 |
| physostigmine transdermally (1.5 $cm^2$/kg) + Scopoderm ® | 1/10 |

TABLE 2

Efficacy of a physostigmine or combined physostigmine-scopolamine-pretreatment in guinea pigs against a soman load and additional post-exposure therapy with atropine sulfate and obidoxime chloride (in each case 10 mg/kg body weight IM, 1 min. after soman).

| Pretreatment | Efficacy index*) (fiduciary limits) |
| --- | --- |
| pyridostigmine transdermally (1.5 $cm^2$/kg) | 3.45 (3.00; 3.95) |
| pyridostigmine transdermally (1.5 $cm^2$/kg) + Alzet ® -scopolamine 4.5 ng $kg^{-1}h^{-1}$ | 3.70 (3.65; 4.50) |

*) efficacy index = $\dfrac{LD_{50} \text{ with treatment}}{LD_{50} \text{ without treatment}}$ In test series using two different physostigmine formulations, the combined pretreatment with transdermal physostigmine and Scopoderm®TTS without post-exposure therapy resulted in efficacy indices of 2.11 (1.71; 2.60) and 2.27 (1.86; 2.79), respectively.

The pharmacokinetics of transdermally administered physostigmine and scopolamine was tested on pigs. Within a period of 5 to 6 h, the plasma concentration rose to a level which lasted for 72 h. In order to examine the effectiveness against an intravenous soman load in pigs, physostigmine skin patches (0.5 cm²/kg) were used which resulted in plasma concentrations of 1.1±0.1 ng/ml (16±3% inhibition of the cholinesterase activity in the total blood) after 48 h. The Scopoderm®-TTS caused scopolamine concentrations in the plasma of 0.18±0.06 ng/ml (n=9) after 24 h. The following results (Table 3) were obtained for a load of 2.5 $LD_{50}$ soman without additional post-exposure therapy:

TABLE 3

Protective action of the physostigmine and physostigmine-scopolamine pretreatment in pigs against a load of 2.5 $LD_{50}$ soman IV, without additional post-exposure therapy

| Pretreatment | Lethality rate | Mean recovery time *) (min.) |
|---|---|---|
| Scopoderm ®TTS | 4/4 | — |
| Physostigmine transdermally (0.5 cm²/kg) | 1/4 | 146 |
| Physostigmine transdermally (0.5 cm²/kg) + Scopoderm ®TTS | 2/5 | 29 |

*) Recovery time = period until the surviving animals are able to stand and walk.

When the pigs were not subjected to 2.5 $LD_{50}$ but to 4 $LD_{50}$ soman IV after the transdermal physostigmine-scopolamine-pretreatment, and when a post-exposure therapy was carried out 20 s later (0.5 mg atropine sulfate and 3 mg obidoxime chloride/kg body weight, IM), 3 out of 5 animals survived, with the surviving animals having higher physostigmine and scopolamine concentrations than the dead ones. When the post-exposure therapy additionally comprised loprazolam (0.2 mg/kg, IM) all of the 5 animals survived, however, recovery of 2 animals was insufficient, exemplifying the disadvantages of the benzodiazepine administration.

Clinical Tolerance Studies

The tolerance of physostigmine skin patches was tested with 11 voluntary test persons (age 29±2 years) under double-blind-conditions as against placebo and additional use of Scopoderm® TTS. With the physostigmine concentrations in the plasma amounting to 0.3±0.1 ng/ml after 48 h, and the scopolamine concentrations amounting to 0.07±0.01 ng/ml, scopolamine proved to be effective in suppressing the undesired effects caused by physostigmine, in particular nausea and vomiting. Statistically significant changes in behavior and performance could not be detected in case of the combined physostigmine-scopolamine-treatment. Accordingly, the object according to the present invention is achieved, i.e., to develop an administration form comprising at least one parasympathomimetic and at least one parasympatholytic, without occurrence of the side effects typical for these substances.

What is claimed is:

1. A pharmaceutical formulation for the long term prophylaxis of a poisoning caused by organophosphorus cholinesterase inhibitors, said pharmaceutical formulation containing a mixture of active substances comprising at least one parasympathomimetic and at least one parasympatholytic in an oral or parenteral administration containing said active substances in a manner showing a depot effect for a controlled release over at least one day.

2. The pharmaceutical formulation according to claim 1, in an administration form for an oral application of the active substance.

3. The pharmaceutical formulation according to claim 1, in an administration form for a parenteral application of the active substance.

4. The pharmaceutical formulation according to claim 1, wherein the parasympatholytic is selected from the group consisting of the tropane alkaloids, their salts and racemic mixtures thereof.

5. The pharmaceutical formulation according to claim 1, in an administration form in which the parasympathomimetic is indirectly effective.

6. The pharmaceutical formulation according to claim 5, wherein the indirectly effective parasympathomimetic comprises acetylcholinesterase inhibitors.

7. The pharmaceutical formulation according to claim 6, wherein the acetylcholinesterase inhibitor comprises physostigmine, heptylphysostigmine, neostigmine, pyridostigmine, tetrahydroacridine, velnacridine, their salts or their racemic mixtures.

8. The pharmaceutical formulation according to claim 1, wherein the parasympathomimetic is scopolamine and/or pharmaceutically acceptable salts thereof and the parasympatholytic is physostigmine and/or pharmaceutically acceptable salt thereof.

9. A prophylactic method of inhibiting a poisoning in an organism caused by an organophosphorus cholinesterase inhibitor, comprising treating said organism before exposure to the organophosphorus cholinesterase inhibitor, orally or parenterally with a pharmaceutical formulation containing a mixture of active substances comprising at least one parasympathomimetic and at least one parasympatholytic in a controlled release administration form, wherein said active substances are present in said controlled release administration form in a manner showing a depot effect.

10. The method according to claim 9, wherein the administration form is for an oral application of the active substance.

11. The method according to claim 9, wherein the administration form is for a parenteral application of the active substance.

12. The method according to claim 9, wherein the parasympatholytic is selected from the group consisting of the tropane alkaloids, their salts and racemic mixtures thereof.

13. The method according to claim 9, wherein the administration form is one in which the parasympathomimetic is indirectly effective.

14. The method according to claim 13, wherein the indirectly effective parasympathomimetic comprises acetylcholinesterase inhibitors.

15. The method according to claim 14, wherein the acetylcholinesterase inhibitor comprises physostigmine, heptylphysostigmine, neostigmine, pyridostigmine, tetrahydroacridine, velnacridine, their salts or their racemic mixtures.

16. The method according to claim 9, wherein the parasympathomimetic is scopolamine and/or pharmaceutically acceptable salts thereof and the parasympatholytic is physostigmine and/or pharmaceutically acceptable salt thereof.

* * * * *